US009061144B2

(12) United States Patent
Fujii et al.

(10) Patent No.: US 9,061,144 B2
(45) Date of Patent: Jun. 23, 2015

(54) SYSTEM FOR IRRADIATING CHARGED PARTICLES AND METHOD FOR IRRADIATING CHARGED PARTICLES

(71) Applicants: HITACHI, LTD., Tokyo (JP); NATIONAL UNIVERSITY CORPORATION HOKKAIDO UNIVERSITY, Hokkaido (JP)

(72) Inventors: Yusuke Fujii, Tokyo (JP); Toru Umekawa, Tokyo (JP); Masumi Umezawa, Tokyo (JP); Hiroki Shirato, Sapporo (JP); Kikuo Umegaki, Sapporo (JP); Naoki Miyamoto, Sapporo (JP); Taeko Matsuura, Sapporo (JP)

(73) Assignees: HITACHI, LTD., Tokyo (JP); NATIONAL UNIVERSITY CORPORATION HOKKAIDO UNIVERSITY, Hokkaido (JP)

( * ) Notice: Subject to any disclaimer, the term of this patent is extended or adjusted under 35 U.S.C. 154(b) by 0 days.

(21) Appl. No.: 14/361,416

(22) PCT Filed: Nov. 14, 2012

(86) PCT No.: PCT/JP2012/079530
§ 371 (c)(1),
(2) Date: May 29, 2014

(87) PCT Pub. No.: WO2013/080800
PCT Pub. Date: Jun. 6, 2013

(65) Prior Publication Data
US 2014/0330066 A1 Nov. 6, 2014

(30) Foreign Application Priority Data
Nov. 30, 2011 (JP) .................................. 2011-262978

(51) Int. Cl.
*G21K 5/04* (2006.01)
*A61N 5/10* (2006.01)

(52) U.S. Cl.
CPC ....... *A61N 5/1068* (2013.01); *A61N 2005/1074* (2013.01); *A61N 2005/1087* (2013.01)

(58) Field of Classification Search
USPC ............. 250/396 R, 397, 492.1, 492.3; 600/1
See application file for complete search history.

(56) References Cited

U.S. PATENT DOCUMENTS

| 5,538,494 A | 7/1996 | Matsuda |
| 2010/0001212 A1* | 1/2010 | Nishiuchi et al. .......... 250/492.3 |

(Continued)

FOREIGN PATENT DOCUMENTS

| JP | 07-303710 A | 11/1995 |
| JP | 09-253226 A | 9/1997 |

(Continued)

OTHER PUBLICATIONS

International Preliminary Report on Patentability received in International Application No. PCT/JP2012/079530 dated Jun. 12, 2014.

*Primary Examiner* — Nicole Ippolito
(74) *Attorney, Agent, or Firm* — Mattingly & Malur, PC

(57) ABSTRACT

A charged particle irradiation system is capable of shortening the irradiation time and the treatment time by performing efficient irradiation even when irregular variation occurs in the irradiation object during the gating irradiation. The extraction of the beam is stopped upon reception of a regular extraction permission end signal which is outputted based on a regular movement signal. An extractable state maintaining function operates upon the reception of the extraction permission end signal. When a preset standby time elapses without receiving an extraction permission start signal again during the standby time, the extractable state maintaining function finishes its operation and a charged particle beam generator decelerates the beam. Also, the extraction of the beam is stopped due to reception of an irregular extraction permission end signal during the irradiation. When the extraction permission start signal is received again during the standby time, the extraction of the beam is restarted.

7 Claims, 14 Drawing Sheets

(56) References Cited

U.S. PATENT DOCUMENTS

2011/0190629 A1* 8/2011 Guenther et al. ............ 600/437
2013/0217946 A1* 8/2013 Balakin ............................ 600/1

FOREIGN PATENT DOCUMENTS

JP          2921433 B2   4/1999
JP          11-319123 A  11/1999

* cited by examiner

SYSTEM FOR IRRADIATING CHARGED PARTICLES AND METHOD FOR IRRADIATING CHARGED PARTICLES

TECHNICAL FIELD

The present invention relates to a charged particle irradiation system and a charged particle irradiation method, and in particular, to a charged particle irradiation system and a charged particle irradiation method for treating a target volume (e.g., tumor) by irradiating the target volume with a charged particle beam.

BACKGROUND ART

There is a well-known method of treating cancer patients, etc. by irradiating a target volume in the patient's body with a charged particle beam (ion beam) such as a proton beam. The system used for the irradiation comprises a charged particle beam generator, a beam transport line, and a treatment room.

The charged particle beam accelerated by the charged particle beam generator reaches an irradiation nozzle (irradiation device) in the treatment room via the beam transport line. The distribution of the charged particle beam is broadened by the irradiation nozzle and an irradiation field suitable for the shape of the target volume is formed in the patient's body. The irradiation nozzle may also be equipped with a scanning device which performs the scanning of the charged particle beam in conformity to the shape of the target volume.

Incidentally, since precise irradiation becomes difficult when the target (e.g. target volume) moves due to the patient's respiration or the like, the gating irradiation (irradiating the target only when the target is at a preset position (in an extraction permission area)) is carried out.

In a conventional technology described in Patent Literature 1, the gating irradiation is performed by using a synchrotron as a charged particle beam generator that repeats the injection/acceleration/extraction/deceleration of the beam. The periodic cycle time of the injection/acceleration/extraction of the beam is controlled in order to effectively use the beam in the gating irradiation.

PRIOR ART LITERATURE

Patent Literature

Patent Literature 1: JP-2921433-B

SUMMARY OF THE INVENTION

Problem to be Solved by the Invention

In the gating irradiation, the irradiation is performed in sync with the cycle of the patient's respiration or the like. Although the respiration cycle is generally regular to some extent, the respiration cycle can change irregularly since the respiration is based on the physiological activity of the patient.

In the conventional technology, the charged particle beam generator starts the deceleration immediately when the target deviates from the extraction permission area. Thus, in cases where the target returns to the extraction permission area after deviating from the extraction permission area for a short time (irregular variation), the charged particle beam generator has already started the deceleration and the beam extraction cannot be performed even though the target is within the extraction permission area. Since efficient irradiation is impossible as above, the total irradiation time tends to be long, and consequently, the treatment time is liable to be long in the conventional technology.

It is therefore the primary object of the present invention to provide a charged particle irradiation system and a charged particle irradiation method capable of shortening the irradiation time and the treatment time by performing efficient irradiation even when irregular variation occurs in the irradiation object during the gating irradiation.

Means for Solving the Problem (1) To achieve the above object, the present invention provides a charged particle irradiation system comprising: a charged particle beam generator that repeats injection of charged particles, acceleration of the charged particles, an extractable state after finishing the acceleration, and deceleration of the charged particles; an irradiation nozzle that irradiates an irradiation object with a charged particle beam supplied from the charged particle beam generator; and a control system that controls the charged particle beam generator and the irradiation nozzle, the control system having: an irradiation object state variation signal reception function of receiving signals from an irradiation object monitoring device that monitors state variation of the irradiation object; an extraction permission state setting function of setting an extraction permission state by outputting an extraction permission signal in sync with the state variation of the irradiation object; and an extraction control function of commanding charged particle beam extraction when the charged particle beam generator is in the extractable state and in the extraction permission state, while commanding stoppage of the charged particle beam extraction when the charged particle beam generator is not in the extraction permission state even if the charged particle beam generator is in the extractable state. The control system further has an extractable state maintaining function that operates after the end of the extraction permission state and maintains the extractable state of the charged particle beam generator even after the end of the extraction permission state. The extraction control function commands the charged particle beam extraction again when the extraction permission state starts again during the operation of the extractable state maintaining function, while commanding the deceleration of the charged particle beam generator after the end of the operation of the extractable state maintaining function.

In the conventional technology, when the extraction permission state ends, the extraction control function commands the stoppage of the extraction and immediately commands the deceleration of the charged particle beam generator. Even in cases where the target returns to the extraction permission state in a short time (irregular variation), the charged particle beam generator has already started the deceleration and the beam extraction cannot be performed even though it is in the extraction permission state. Since efficient irradiation is impossible as above, the total irradiation time tends to be long, and consequently, the treatment time is liable to be long in the conventional technology.

In contrast, owing to the operation of the above-described extractable state maintaining function, the extraction control function does not immediately command the deceleration of the charged particle beam generator even when commanding the stoppage of the extraction after the end of the extraction permission state. When the extraction permission state starts again during the operation of the extractable state maintaining function, the extraction control function commands the charged particle beam extraction again.

With this configuration, it is possible to perform efficient irradiation and shorten the irradiation time and the treatment time.

(2) Preferably, in the above charged particle irradiation system (1), the extractable state maintaining function operates for a preset standby time.

With this configuration, the extractable state of the charged particle beam generator is maintained for the preset standby time. When the extraction permission state starts again before the elapse of the preset standby time, the extraction control function commands the charged particle beam extraction again.

(3) Preferably, in the above charged particle irradiation system (2), the extractable state maintaining function starts operating based on a signal that commands termination of the extraction permission state.

(4) Preferably, in the above charged particle irradiation system (2), the extractable state maintaining function starts operating based on a signal that commands the stoppage of the charged particle beam extraction.

The above configurations (3) and (4) set the starting point of the preset standby time.

(5) Preferably, in the above charged particle irradiation system (1), the extractable state maintaining function operates only while the state variation of the irradiation object is within a preset range.

With this configuration, the extractable state of the charged particle beam generator is maintained only while the state variation of the irradiation object is within the preset range. When the extraction permission state starts again while the state variation of the irradiation object is within the preset range, the extraction control function commands the charged particle beam extraction again.

(6) Preferably, in the above charged particle irradiation system (1), the extraction control function commands the stoppage of the charged particle beam extraction after reception of a signal commanding termination of the extraction permission state and after irradiation with a prescribed dose.

With this configuration, in cases of spot irradiation, interruption of the irradiation during the spot irradiation can be eliminated and simpler control can be achieved.

(7) To achieve the above object, the present invention provides a charged particle irradiation method for a charged particle irradiation system equipped with a charged particle beam generator, an irradiation nozzle and a control system that controls the charged particle beam generator, the irradiation nozzle and an irradiation object monitoring device, comprising: an extraction standby step in which the charged particle beam generator repeats injection of charged particles, acceleration of the charged particles, an extractable state after finishing the acceleration, and deceleration of the charged particles; an irradiation object state variation monitoring step in which the irradiation object monitoring device monitors state variation of an irradiation object; an extraction permission state setting step of setting an extraction permission state in sync with the state variation of the irradiation object monitored in the irradiation object state variation monitoring step; an extraction step of extracting a charged particle beam from the charged particle beam generator and having the irradiation nozzle apply the charged particle beam to the irradiation object when the charged particle beam generator is in the extractable state in the extraction standby step and in the extraction permission state due to the extraction permission state setting step; and an extraction stoppage step of stopping the extraction when the charged particle beam generator is not in the extraction permission state due to the extraction permission state setting step even if the charged particle beam generator is in the extractable state in the extraction standby step. The charged particle irradiation method further comprises an extractable state maintaining step of maintaining the extractable state of the charged particle beam generator even after the extraction permission state ends in the extraction permission state setting step. In the extraction step, the charged particle beam is extracted again when the extraction permission state starts again in the extraction permission state setting step during the maintenance of the extractable state by the extractable state maintaining step. In the extraction standby step, the charged particle beam generator decelerates the beam after the end of the maintenance of the extractable state by the extractable state maintaining step.

Effect of the Invention

According to the present invention, the irradiation time and the treatment time can be shortened by performing efficient irradiation even when irregular variation occurs in the irradiation object during the gating irradiation.

MODE FOR CARRYING OUT THE INVENTION

Figure 1:
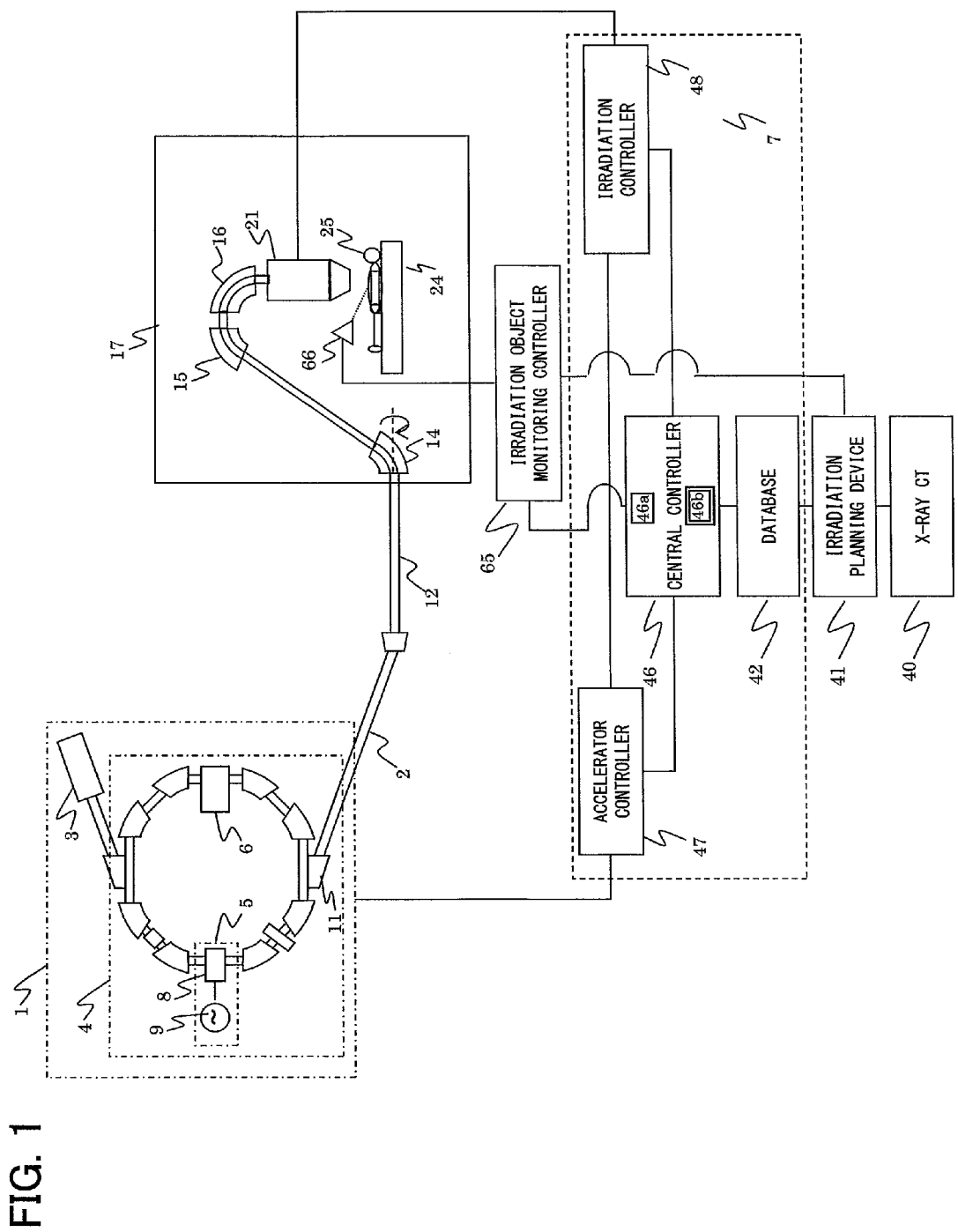
FIG. 1 is a schematic block diagram showing the overall configuration of a charged particle irradiation system (first embodiment).

Referring now to the drawings, a description will be given in detail of preferred embodiments of the present invention.
<First Embodiment>
Configuration FIG. 1 is a schematic block diagram showing the overall configuration of a charged particle irradiation system. The charged particle irradiation system comprises a charged particle beam generator 1, a beam transport line 2, a radiation treatment room 17, a control system 7, an irradiation object monitoring controller 65, and an irradiation object monitoring device 66. Further, an X-ray CT 40 and an irradiation planning device 41 are arranged as equipment related to the charged particle irradiation system.

The charged particle beam generator 1 includes an ion source (unshown), a linear accelerator 3 (charged particle beam preaccelerator) and a synchrotron 4. The synchrotron 4 includes a radiofrequency wave application device 5 and an accelerator 6. The radiofrequency wave application device 5 includes a radiofrequency power supply 9 and radiofrequency electrodes 8 arranged in the closed orbit of the synchrotron 4. The radiofrequency power supply 9 is connected to the radiofrequency electrodes 8 via a switch (unshown). The accelerator 6 includes a radiofrequency acceleration cavity (unshown) arranged in the closed orbit of the ion beam and a radiofrequency power supply (unshown) for applying radiofrequency electric power to the radiofrequency acceleration cavity. An extraction deflector 11 connects the synchrotron 4 to the beam transport line 2.

The beam transport line 2 includes a beam path 12, quadrupole magnets (unshown), and bending magnets 14, 15 and 16. The beam path 12 is connected to an irradiation nozzle (irradiation device) 21 which is arranged in the treatment room 17.

A rotating gantry (unshown) is installed in the treatment room 17. The irradiation nozzle 21 and the bending magnets 15 and 16 as parts of the beam transport line 2 are arranged in the rotating gantry. A treatment bed (referred to as a "couch 24") and the irradiation object monitoring device 66 for measuring the movement of the irradiation object 25 on the bed are arranged inside the rotating gantry.

The rotating gantry is configured to be rotatable by a motor. The bending magnets 15 and 16 and the irradiation nozzle 21 rotate along with the rotation of the gantry. Owing to the rotation, the irradiation object 25 can be irradiated from any direction in a plane orthogonal to the rotation axis of the gantry.

Figure 2:
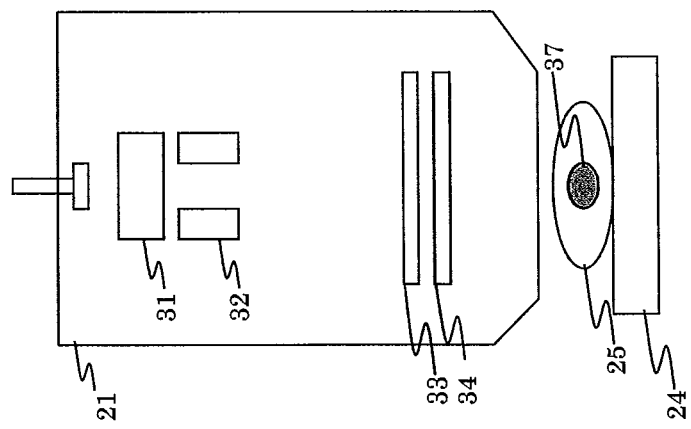
FIG. 2 is a schematic diagram showing the configuration of an irradiation nozzle.

FIG. 2 is a schematic diagram showing the configuration of the irradiation nozzle 21. The irradiation nozzle 21 includes a scanning magnet 31, a scanning magnet 32, a beam position monitor 33, and a dose monitor 34. In the charged particle irradiation system of this embodiment, the irradiation nozzle 21 is equipped with two scanning magnets 31 and 32 and the irradiation position is changed by deflecting the ion beam in two directions (X direction, Y direction) in a plane orthogonal to the beam propagation direction. The beam position monitor 33 measures the position and the broadening of the ion beam. The dose monitor 34 measures the amount of the irradiating ion beam. An irradiation target 37 exists in the irradiation object 25. By the irradiation with the ion beam, a dose distribution covering the irradiation target 37 is formed inside the irradiation object 25. In the treatment of cancer or the like, the irradiation object 25 is a human (patient) and the irradiation target 37 is a tumor (target volume).

Figure 3A:
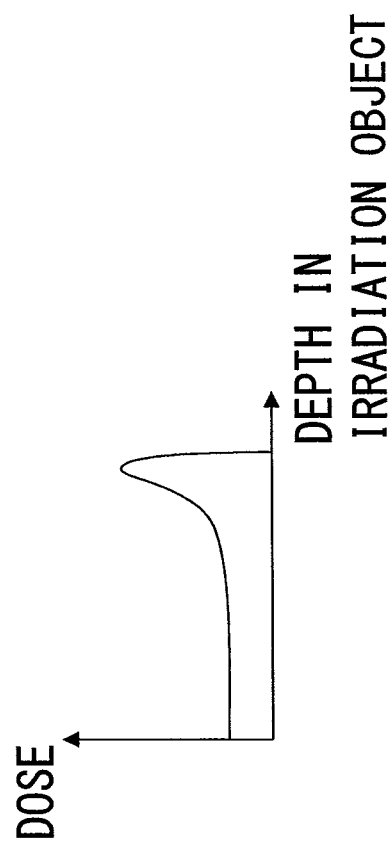
FIG. 3A is a graph for explaining the relationship between the depth of the target and the energy of the ion beam.
Figure 3B:
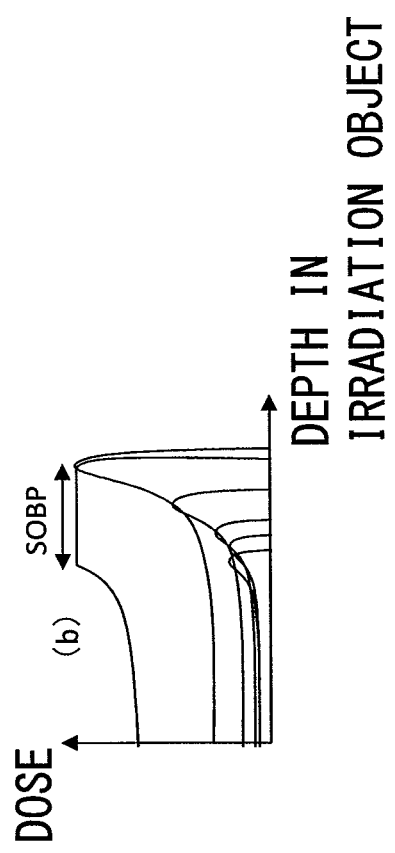
FIG. 3B is a graph for explaining the relationship between the depth of the target and the energy of the ion beam.

FIGS. 3A and 3B are graphs for explaining the relationship between the depth of the target and the energy of the ion beam. FIG. 3A indicates a dose distribution formed in the irradiation object by a single-energy ion beam as a function of the depth, while FIG. 3B indicates a dose distribution formed in the irradiation object by several ion beams of different energy levels as a function of the depth. The peak shown in FIG. 3A is called a "Bragg peak". Since the position of the Bragg peak changes depending on the energy, irradiation of the irradiation target at the Bragg peak position is possible by adjusting the energy of the ion beam to suit the depth of the irradiation target. The irradiation target has a certain thickness in the depth direction, whereas the Bragg peak is a sharp peak. Therefore, a uniform high-dose region (SOBP (spread-out Bragg peak)) having the same thickness in the depth direction as the irradiation target is formed by superimposing several Bragg peaks as shown in FIG. 3B, by performing the irradiation by use of several ion beams of different energy levels in an appropriate intensity ratio.

Figure 4:
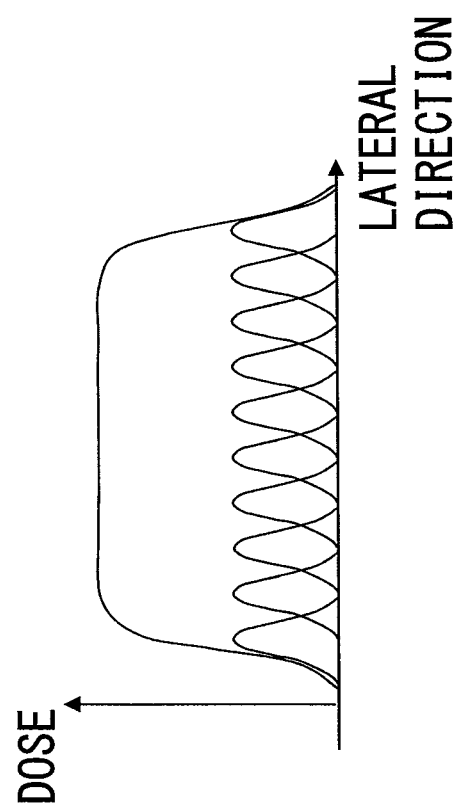
FIG. 4 is a graph for explaining the relationship between the ion beam and the lateral dimension of the irradiation target in a direction orthogonal to the beam axis (direction parallel to an XY plane).

FIG. 4 is a graph for explaining the relationship between the ion beam and the lateral dimension of the irradiation target in a direction orthogonal to the beam axis (direction parallel to the XY plane). Each direction orthogonal to the beam axis will hereinafter be referred to as a "lateral direction". After entering the irradiation nozzle 21, the ion beam is scanned (deflected) by the two scanning magnets 31 and 32 arranged orthogonal to each other and reaches an intended position in the lateral direction. The broadening of the ion beam in the lateral direction can be approximated by the shape of a Gaussian distribution. If a plurality of identical Gaussian distributions are arranged at even intervals while setting the interval substantially at the standard deviation of the Gaussian distribution, the distribution formed by the superimposed (overlapped) Gaussian distributions has a uniform region. Each of the Gaussian distribution-like dose distributions arranged as above is referred to as "spot". A dose distribution that is uniform in the lateral direction can be formed by arranging a plurality of spots at even intervals by scanning the ion beam.

As explained above, a uniform irradiation field can be formed by the beam scan in the lateral direction by using the scanning magnets and the Bragg peak shift in the depth direction by changing the beam energy. Incidentally, a unit of the irradiation field, irradiated with the same energy and having a certain broadening in the lateral direction due to the ion beam scan by the scanning magnets, is referred to as a "slice".

Returning to FIG. 1, the irradiation planning device 41 and an accompanying configuration will be explained below.

Before the irradiation of the irradiation target 37 with the ion beam is carried out, the irradiation planning device 41 determines parameters necessary for the irradiation. The parameters are determined as explained below.

The irradiation object 25 is previously image-captured by the X-ray CT device 40. Further, a patient movement signal outputted from an unshown device (equivalent to the irradiation object monitoring device 66) attached to the X-ray CT device 40 is acquired. The X-ray CT device 40 generates image data of the irradiation object 25 based on the acquired imaging data and sends the generated image data to the irradiation planning device 41. The irradiation planning device 41 displays the received image data on the screen of a display device (unshown). When a region that should be irradiated is specified on the image by the operator, the irradiation planning device 41 generates data necessary for the irradiation, calculates a dose distribution that is expected in the irradiation by use of the data, and displays the calculated dose distribution on the display device. The region that should be irradiated is specified so as to cover the irradiation target 37. The irradiation planning device 41 calculates and determines an irradiation object setting position (position where the irradiation object 25 should be set), a gantry angle, and irradiation parameters with which the dose distribution can be formed in the specified region. Further, the irradiation planning device 41 determines the initial position of the couch 24 and also determines the extraction permission area based on the acquired movement signal.

The irradiation parameters include the energy of the ion beam, positional information (X coordinate, Y coordinate) in a plane orthogonal to the beam axis, and a target irradiation amount of the ion beam for the irradiation of each position. Specifically, the irradiation planning device 41 divides the irradiation target (target volume) 37 into a plurality of slices arranged in the depth direction based on patient information inputted by the operator and determines the number N of necessary slices (slice count N). The irradiation planning device 41 also determines the ion beam energy $E_i$ suitable for the irradiation of each slice (slice No. i) according to the depth of each slice. Further, according to the shape of each slice, the irradiation planning device 41 determines the number $N_i$ of irradiation spots to be irradiated with the ion beam (spot count $N_i$), spot numbers j, the irradiation position $(X_{ij}, Y_{ij})$ of each spot, and the target irradiation amount $D_{ij}$ for each spot.

The irradiation planning device 41 sends the information (data) determined as above to a database 42. The database 42 records the data outputted from the irradiation planning device 41.

Figure 5:
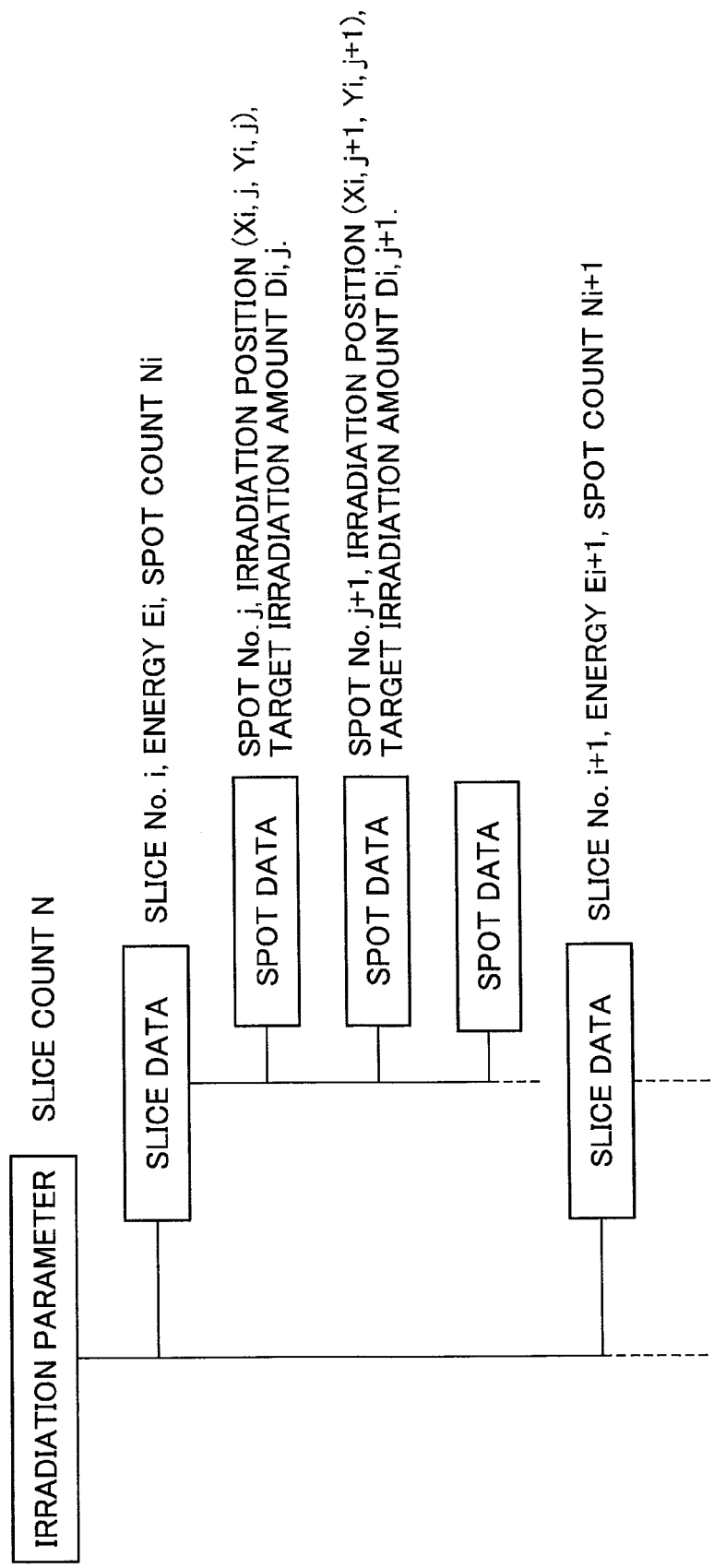
FIG. 5 shows data structure of irradiation parameters registered in a database.

FIG. 5 shows the data structure of the irradiation parameters registered in the database 42. The irradiation parameters include the slice count N and data regarding each slice. The data regarding each slice includes the slice number i, the energy $E_i$, the spot count $N_i$, and data regarding each spot. The data regarding each spot includes the spot number j, the irradiation position $(X_{ij}, Y_{ij})$, and the target irradiation amount $D_{ij}$.

Returning to FIG. 1, a configuration related to the control system of the charged particle irradiation system will be explained below.

The irradiation object monitoring device 66 is an instrument capable of measuring the movement of the target 37 or an amount that changes in conjunction with the movement. For example, the irradiation object monitoring device 66 may be implemented by a laser distance meter for measuring the movement of the body surface of the patient, an aeroplethysmograph for measuring the amount of the patient's exhalation, a device for measuring the pressure in a belt wound around the patient's abdomen, etc. In order to use these methods, it is necessary to previously (before the treatment) determine the relationship between the output of the measuring instrument and the position of the target. The irradiation object monitoring device 66 may also be implemented by a device that determines the position of a marker inserted in the vicinity of the target 37 (or the position of the target 37 itself) by means of roentgenography. Incidentally, the irradiation object monitoring device 66 may be provided either as a component of the charged particle irradiation system or as an external instrument added to the charged particle irradiation system.

The irradiation object monitoring device 66 is controlled by the irradiation object monitoring controller 65. The irradiation object monitoring controller 65 receives a movement signal from the irradiation object monitoring device 66 and outputs an extraction permission signal based on comparison between the movement signal and the extraction permission area. The extraction permission area, which has been set previously, is sent from the irradiation planning device 41. The extraction permission area may also be designated by the operator. The extraction permission signal includes an extraction permission start signal and an extraction permission end signal. The state (period) between the outputting of the extraction permission start signal and the outputting of the extraction permission end signal by the irradiation object monitoring controller 65 is set as an extraction permission state. The irradiation object monitoring controller 65 may also be provided as a component of the control system 7.

The control system 7 includes the database (data storage device) 42, a central controller 46, an accelerator controller 47, and an irradiation controller 48. The database 42 is connected to the irradiation planning device 41. The data necessary for the irradiation generated by the irradiation planning device 41 are stored in the database 42.

The central controller 46 is connected to the accelerator controller 47, the irradiation controller 48 and the database 42. The central controller 46 receives data from the database 42, sends necessary information to the accelerator controller 47 and the irradiation controller 48, and thereby controls the controllers 47 and 48.

The accelerator controller 47 is connected to the charged particle beam generator 1, the beam transport line 2 and the rotating gantry to control them. For example, the accelerator controller 47 performs the control so that the charged particle beam generator 1 repeats the injection of the charged particles, the acceleration of the charged particles, an extractable state after finishing the acceleration, and the deceleration of the charged particles and so that the charged particle beam generator 1 extracts (emits) the charged particle beam when the charged particle beam generator 1 is in the extractable state. The irradiation controller 48 controls the amounts of excitation currents flowing through the scanning magnets 31 and 32 while also processing the monitoring signals inside the irradiation nozzle 21.

The central controller 46 has various computation functions. A gating irradiation function 46a is one of the computation functions of the central controller 46. The gating irradiation function 46a commands the charged particle beam extraction when the charged particle beam generator 1 is in the extractable state and in the extraction permission state. The gating irradiation function 46a commands stoppage of the charged particle beam extraction when the charged particle beam generator 1 is not in the extraction permission state even if the charged particle beam generator 1 is in the extractable state.

The central controller 46 has an extractable state maintaining function 46b as a characteristic function of this embodiment. The extractable state maintaining function 46b waits on standby for a preset standby time when the extraction permission end signal is received from the irradiation object monitoring controller 65. Consequently, the extractable state of the charged particle beam generator 1 is maintained for the preset standby time.

The gating irradiation function 46a commands the charged particle beam extraction again when the extraction permission start signal is received again from the irradiation object monitoring controller 65 during the preset standby time. If the extraction permission start signal is not received again, after the elapse of the preset standby time, the gating irradiation function 46a commands the accelerator controller 47 to decelerate the charged particle beam generator 1.

The details of the processing by the gating irradiation function 46a and the extractable state maintaining function 46b will be explained below referring to control flow charts of FIGS. 6 and 7.

Control

In order to carry out the irradiation control, the irradiation object 25 is set on the couch 24, and the couch 24 with the irradiation object 25 is moved to a position specified by the irradiation planning device 41.

Figure 6:
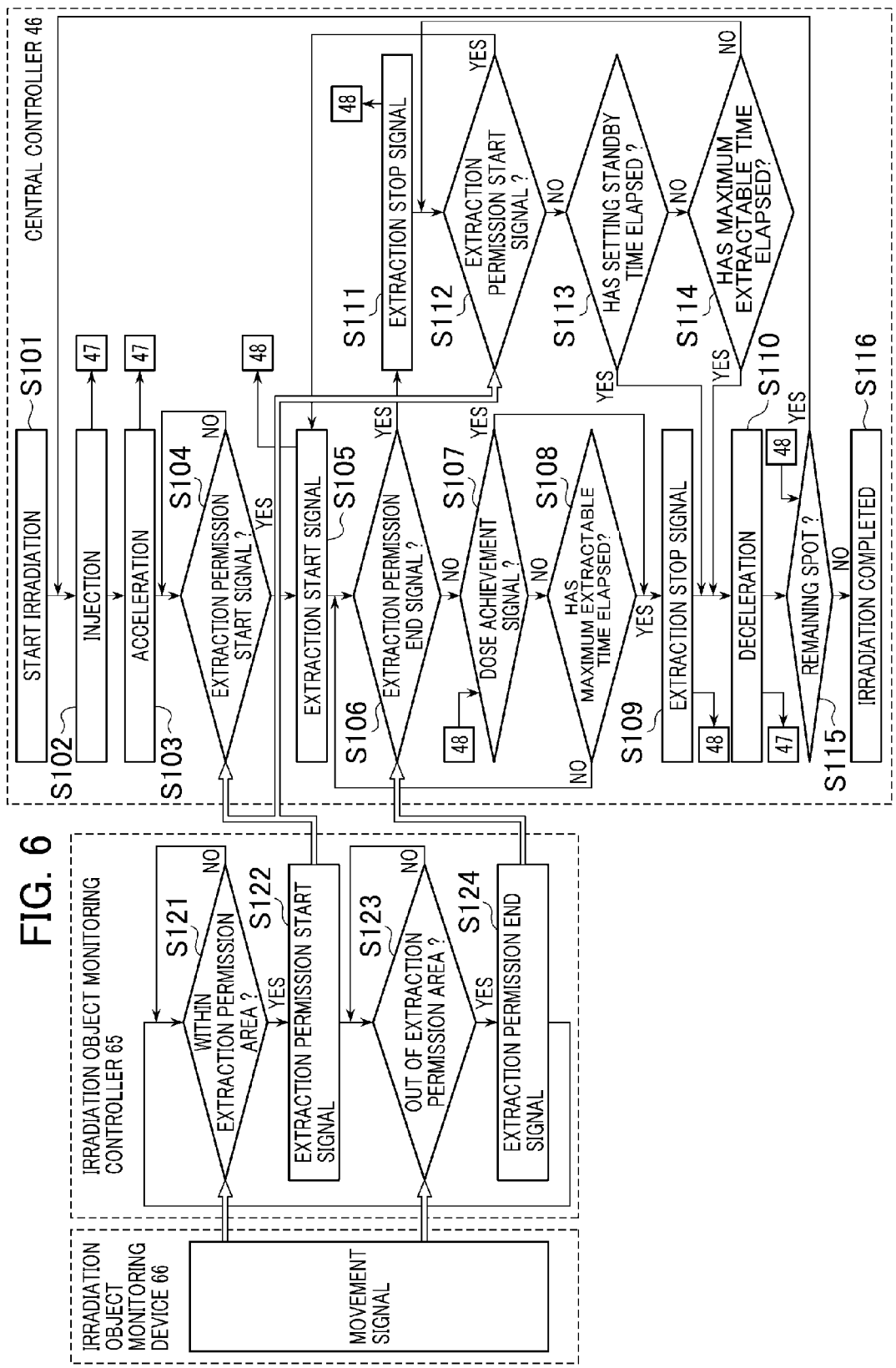
FIG. 6 is a control flow chart showing the details of processing by an irradiation object monitoring controller and a central controller.

FIG. 6 is a control flow chart showing the details of the processing by the irradiation object monitoring controller 65 and the central controller 46, wherein details of the processing by the accelerator controller 47 and the irradiation controller 48 are shown in simplified manners for convenience of the explanation.

The details of the processing by the irradiation object monitoring controller 65 will be explained below.

The irradiation object monitoring controller 65 compares the movement signal acquired from the irradiation object monitoring device 66 with the extraction permission area (step S121). The extraction permission area may either be specified by the operator before the irradiation or previously generated by the irradiation planning device 41.

When the movement signal enters the extraction permission area in the step S121, the irradiation object monitoring controller 65 sends the extraction permission start signal to the central controller 46 (step S122). When the movement signal is out of the extraction permission area, the irradiation object monitoring controller 65 waits on standby until the judgment in the step S121 becomes affirmative.

Thereafter, the irradiation object monitoring controller 65 compares the movement signal acquired from the irradiation object monitoring device 66 with the extraction permission area (step S123). When the movement signal deviates from the extraction permission area in the step S123, the irradiation object monitoring controller 65 sends an extraction permission end signal to the central controller 46 (step S124).

Thereafter, this control process is repeated until the completion of the irradiation. The state (period) between the outputting of the extraction permission start signal and the outputting of the extraction permission end signal by the irradiation object monitoring controller 65 is set as the extraction permission state.

Next, the details of the processing by the central controller 46 will be explained below.

The central controller 46 receives the operator's instruction and sends an irradiation start signal to the accelerator controller 47 and the irradiation controller 48 (step S101). Further, the central controller 46 sends an injection signal to the accelerator controller 47 for the injection of the beam (step S102) and sends an acceleration signal to the accelerator controller 47 for the acceleration of the beam (step S103).

A brief explanation of the processing by the accelerator controller 47 corresponding to the steps S101-S103 is inserted here.

The accelerator controller 47 receives the irradiation parameters and gantry angle information from the database 42 via the central controller 46. The accelerator controller 47 moves the rotating gantry to a desired gantry angle according to the received gantry angle information. Further, based on the irradiation parameters, the accelerator controller 47 sets the values of the excitation currents for exciting the magnets of the synchrotron 4 and the beam transport line 2, the value of the radiofrequency wave to be applied by the radiofrequency wave application device 5, and the value of the radiofrequency wave to be applied to the accelerator 6, each value corresponding to the ion beam energy Ei for each slice.

Upon receiving the injection signal, the accelerator controller 47 activates the ion source. Ions (e.g., protons (or carbon ions)) generated in the ion source are injected into the linear accelerator 3. The linear accelerator 3 accelerates the ions and emits the accelerated ions. The ion beam from the linear accelerator 3 is injected into the synchrotron 4.

Upon receiving the acceleration signal, the accelerator controller 47 accelerates the ion beam (injected into the synchrotron 4 from the linear accelerator 3) up to the ion beam energy E1 for the slice No. 1 by controlling the accelerator 6 and the magnets of the synchrotron 4. In short, the accelerator controller 47 accelerates the ion beam up to intended energy by controlling the charged particle beam generator 1. The acceleration is performed by applying the radiofrequency wave from the radiofrequency power supply to the radiofrequency acceleration cavity (i.e., by giving energy to the ion beam circulating in the synchrotron 4 by using the radiofrequency electric power). Meanwhile, the accelerator controller 47 controls the levels of excitation of the magnets of the beam transport line 2 so that the accelerated ion beam can be transported to the irradiation nozzle 21. This state is referred to as the extractable state.

The explanation returns to that of the processing by the central controller 46.

Upon recognizing the extractable state, the central controller 46 judges whether or not the extraction permission start signal has been received from the irradiation object monitoring controller 65 (step S104). If the extraction permission start signal has not been received in the step S104, the central controller 46 waits on standby until the extraction permission start signal is received. Upon receiving the extraction permission start signal, the central controller 46 sends an extraction start signal to the irradiation controller 48 (step S105).

Thereafter, the central controller 46 waits on standby (commands continuation of the extraction) until any one of judgments in step S106 (whether or not the extraction permission end signal has been received), step S107 (whether or not a dose achievement signal has been received) and step S108 (whether or not a maximum extractable time has elapsed) becomes affirmative.

When the judgment in the step S107 or S108 is affirmative, the central controller 46 sends an extraction stop signal to the irradiation controller 48 (step S109) and sends a deceleration signal to the accelerator controller 47 for the deceleration of the beam (step S110). Incidentally, the dose achievement signal judged in the step S107 is a signal received from the irradiation controller 48. The maximum extractable time judged in the step S108 is the maximum time for which the accelerated beam can be maintained in the extractable state. The maximum extractable time includes the time for which the beam is extracted.

Control that is characteristic of this embodiment will be explained below.

During the continuation of the extraction, the central controller 46 judges whether or not the extraction permission end signal has been received from the irradiation object monitoring controller 65 (step S106). If the extraction permission end signal has been received in the step S106, the central controller 46 sends the extraction stop signal to the irradiation controller 48 (step S111).

Thereafter, the central controller 46 waits on standby (commands continuation of the stoppage of the extraction) until any one of judgments in step S112 (whether or not the extraction permission start signal has been received again), step S113 (whether or not the preset standby time has elapsed) and step S114 (whether or not a maximum extractable time has elapsed) becomes affirmative.

If the extraction permission start signal from the irradiation object monitoring controller 65 has been received again in the step S112, the central controller 46 returns to the step S105 and sends the extraction start signal again to the irradiation controller 48.

If the preset standby time has elapsed in the step S113 since the reception of the extraction permission end signal, the central controller 46 advances to step S110 and sends the deceleration signal to the accelerator controller 47 to decelerate the beam. The preset standby time is the maximum standby time from the reception of the extraction permission end signal to the start of the deceleration. The preset standby time may either be set by the operator before the irradiation or previously set by the irradiation planning device 41. The preset standby time may either be changed from irradiation to irradiation or fixed at the originally determined value.

If the maximum extractable time has elapsed in the step S114, the central controller 46 advances to the step S110.

A brief explanation of the processing by the accelerator controller 47 corresponding to the step S110 is inserted here.

Upon receiving the deceleration signal, the accelerator controller 47 lowers the levels of excitation of the magnets of the synchrotron 4 for the deceleration and preparation for the injection and thereby sets the synchrotron 4 in a state in which the beam from the linear accelerator 3 can be injected.

The explanation returns to that of the processing by the central controller 46.

The central controller 46 refers to the irradiation controller 48 and judges whether or not there is a remaining spot (which has not been irradiated yet) among the spots described in the irradiation parameters (step S115). If there is a remaining spot, the central controller 46 returns to the step S102 (injection of the beam) and accelerates the beam up to the energy for the spot to be irradiated next (step S103). If there is no remaining spot, the central controller 46 sends an irradiation completion signal to the accelerator controller 47 and the irradiation controller 48 (step S116).

Figure 7:
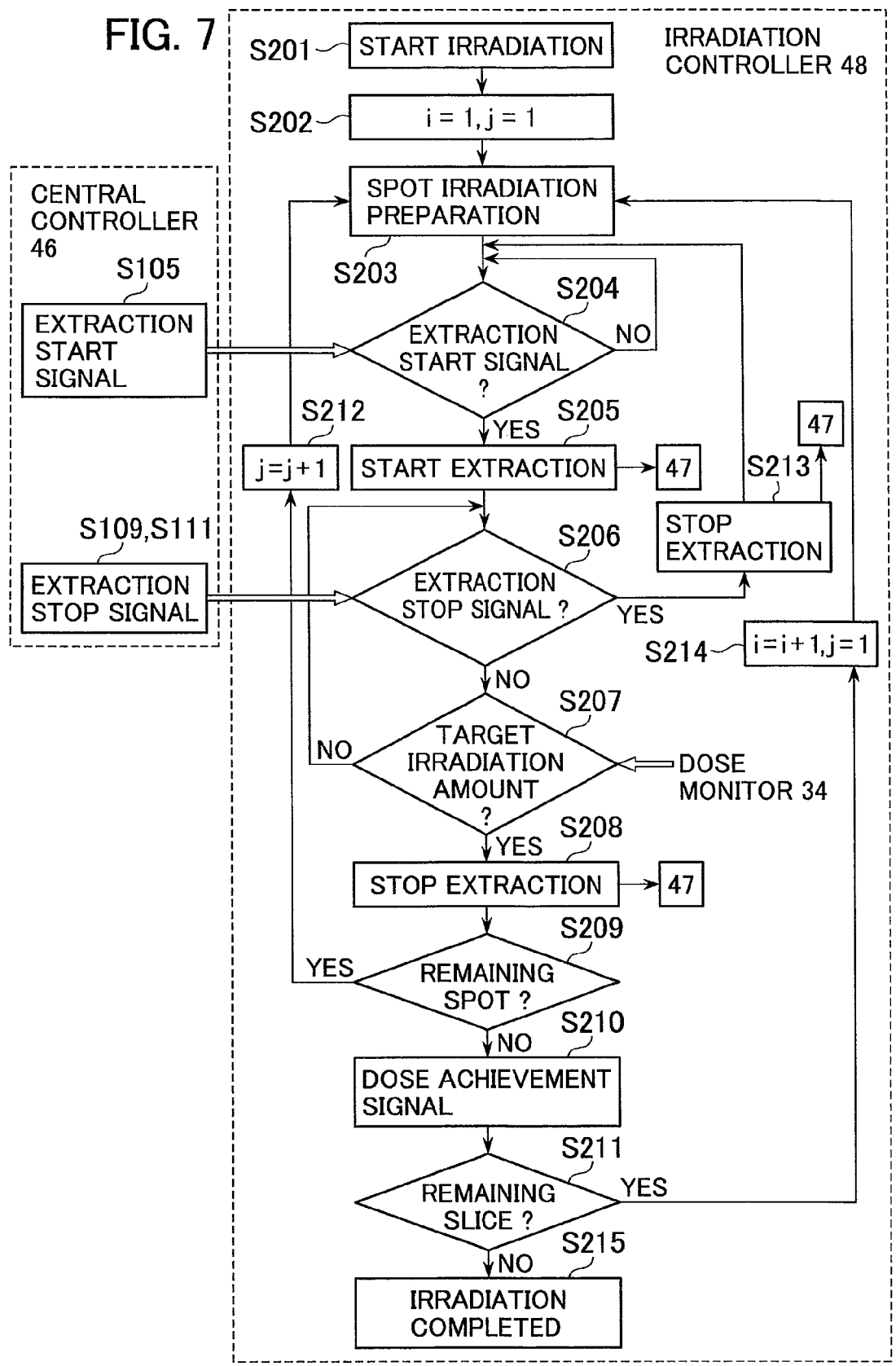
FIG. 7 is a control flow chart showing the details of processing by an irradiation controller.

FIG. 7 is a control flow chart showing the details of the processing by the irradiation controller 48, wherein details of the processing by the central controller 46 and the accelerator controller 47 are shown in simplified manners for convenience of the explanation.

Upon receiving the irradiation start signal from the central controller 46, the irradiation controller 48 starts controlling the irradiation nozzle 21 (step S201). The irradiation is started from slice No. i=1 and spot No. j=1 (step S202).

The irradiation controller 48 excites the scanning magnets 31 and 32 with the excitation current values corresponding to the slice No. 1 and the spot No. 1 calculated by the central controller 46, and the preparation for the irradiation is thereby completed (step S203).

After completing the irradiation preparation, the irradiation controller 48 judges whether or not the extraction start signal from the central controller 46 has been received (step S204). If the extraction start signal has not been received in the step S204, the irradiation controller 48 waits on standby until the extraction start signal is received. Upon receiving the extraction start signal, the irradiation controller 48 sends an extraction signal to the accelerator controller 47 (step S205).

A brief explanation of the processing by the accelerator controller 47 corresponding to the step S205 is inserted here.

Upon receiving the extraction signal, the accelerator controller 47 starts the extraction of the ion beam from the synchrotron 4 by controlling the radiofrequency wave application device 5. Specifically, the accelerator controller 47 connects the aforementioned switch and thereby makes the radiofrequency wave application device 5 apply the radiofrequency wave to the ion beam. The ion beam which has been circulating in the synchrotron 4 within the stability limit shifts to the outside of the stability limit and is extracted from the synchrotron 4 through the extraction deflector 11. The extracted ion beam passes through the beam transport line 2 and enters the irradiation nozzle 21.

Inside the irradiation nozzle 21, the ion beam is scanned by the scanning magnets 31 and 32 and then passes through the beam position monitor 33 and the dose monitor 34. Thereafter, the ion beam reaches the irradiation target 37 and stops after giving a prescribed radiation dose to the irradiation target 37.

The explanation returns to that of the processing by the irradiation controller 48.

Thereafter, the irradiation controller 48 waits on standby (commands continuation of the extraction) until any one of judgments in step S206 (whether or not the extraction stop signal has been received) and step S207 (whether or not the target irradiation amount has reached) becomes affirmative.

In the step S207, the irradiation controller 48 counts the irradiation amount with a dose counter based on a signal received from the dose monitor 34. When the value of the dose counter reaches the target irradiation amount, the irradiation controller 48 judges that the irradiation of the spot j (spot No. j) is completed and sends a stop signal to the accelerator controller 47 to stop the extraction (step S208).

Then, the irradiation controller 48 judges whether or not there is a remaining spot in the same slice (step S209). If there is a remaining spot (j<Ni) in the step S209, the irradiation controller 48 increments the value of j by 1 (step S212) and returns to the step S203 to irradiate the next spot. If there is no remaining spot (j=Ni) after repeating the spot irradiation, the irradiation controller 48 judges that the irradiation of the slice i (slice No. i) is completed and sends the dose achievement signal to the central controller 46 (step S210).

Then, the irradiation controller 48 judges whether or not there is a remaining slice (step S211). If there is a remaining slice (i<N) in the step S211, the irradiation controller 48 increments the value of i by 1 (step S214) and returns to the step S203 to irradiate the next slice. If there is no remaining slice (i=N) after repeating the slice irradiation, the irradiation controller 48 judges that the irradiation of all the slices is completed. At this point, the irradiation is completed (step S215).

In gating irradiation like the one executed in this embodiment, the stop signal is sent to the accelerator controller 47 to stop the extraction (step S213) when the judgment in the step S206 becomes affirmative, that is, when the extraction stop signal is received. Thereafter, the irradiation controller 48 returns to the step S204 and waits on standby until the next extraction start signal is received.

A brief explanation of the processing by the accelerator controller 47 corresponding to the steps S208 and S213 is inserted here.

Upon receiving the stop signal, the accelerator controller 47 stops the extraction by controlling the radiofrequency wave application device 5. Specifically, the extraction of the ion beam from the synchrotron 4 is stopped by stopping the application of the radiofrequency wave by disconnecting the switch between the radiofrequency power supply 9 and the radiofrequency electrodes 8.

Correspondence with Claims

The irradiation object monitoring controller 65 and the steps S122 and S124 executed by the irradiation object monitoring controller 65 constitute an extraction permission state setting function of setting the extraction permission state by outputting the extraction permission start signal and the extraction permission end signal in sync with state variation of the irradiation object 25.

The gating irradiation function 46a of the central controller 46 and the steps S104, S105, S106 and S111 executed by the central controller 46 constitute an extraction control function of commanding the charged particle beam extraction when the charged particle beam generator 1 is in the extractable state and in the extraction permission state, while commanding the stoppage of the charged particle beam extraction when the charged particle beam generator 1 is not in the extraction permission state even if the charged particle beam generator 1 is in the extractable state.

The extractable state maintaining function 46b of the central controller 46 and the step S113 executed by the central controller 46 constitute an extractable state maintaining function that operates for the preset standby time after the reception of the extraction permission end signal and maintains the extractable state of the charged particle beam generator 1 even after the end of the extraction permission state.

The gating irradiation function 46a of the central controller 46 and the steps S112, S105 and S110 executed by the central controller 46 constitute an extraction control function of commanding the charged particle beam extraction again when the extraction permission state starts again during the operation of the extractable state maintaining function 46b (i.e., during the standby time), while commanding the deceleration of the charged particle beam generator 1 after the end of the operation of the extractable state maintaining function 46b (i.e., after the elapse of the preset standby time).

Operation

The operation of the charged particle irradiation system according to this embodiment will be explained below in regard to three different cases 1-3.

Figure 8:
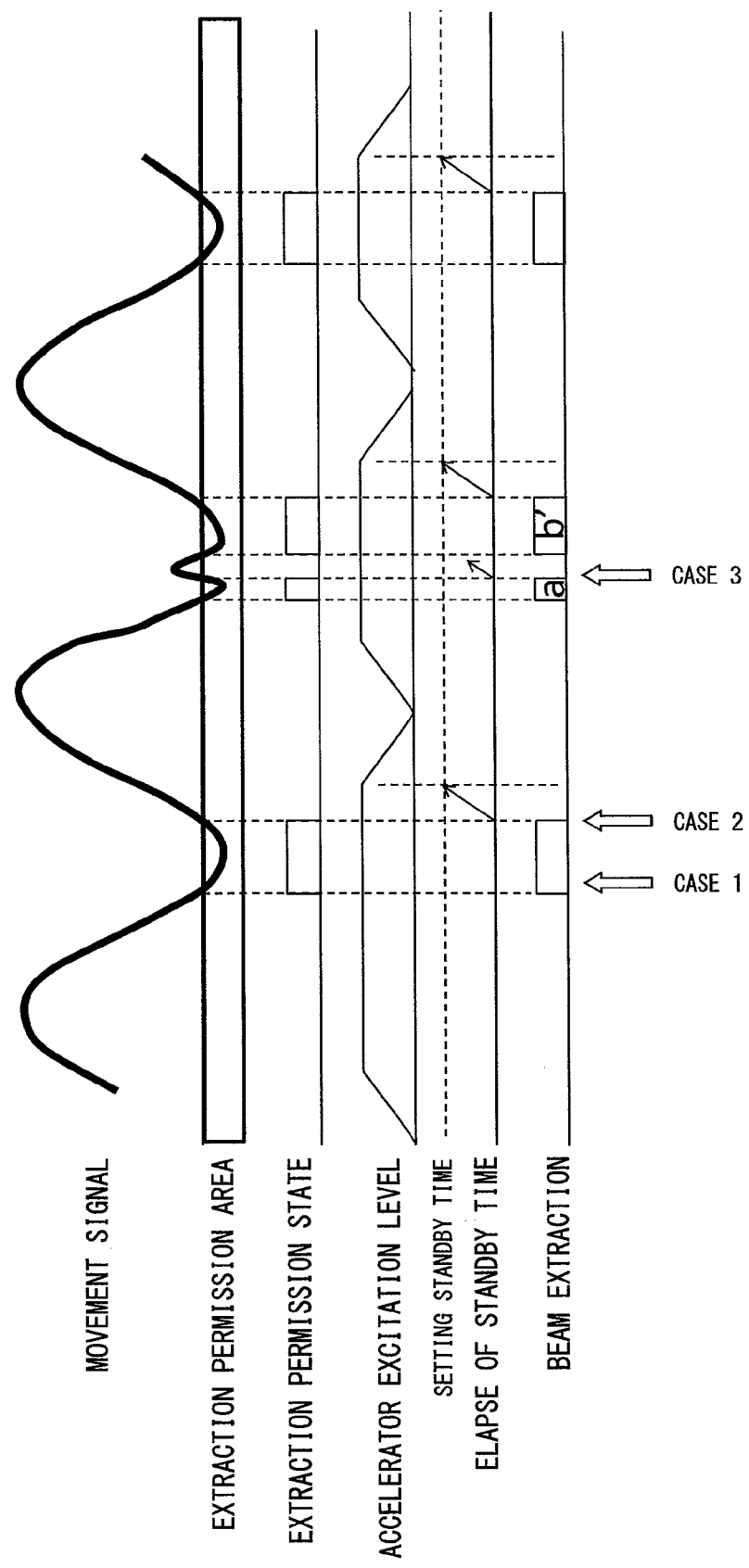
FIG. 8 is a conceptual diagram for explaining the operation of the charged particle irradiation system.

FIG. 8 is a conceptual diagram for explaining the operation of the charged particle irradiation system, wherein the horizontal axis represents the time and the vertical axis represents (from top to bottom) the movement signal, the extraction permission area, the extraction permission state, the accelerator excitation level, the elapse of the standby time, and the beam extraction.

The extraction permission state is set in periods during which the movement signal representing the position of the target 37 is within the extraction permission area. Each extraction permission state is set as a state (period) from the outputting of the extraction permission start signal to the outputting of the extraction permission end signal.

The accelerator excitation level represents the level of excitation of the bending magnets of the synchrotron 4. It is possible to inject the beam into the synchrotron 4 when the excitation level is low, accelerate the beam, and thereafter extract the beam from the synchrotron 4 in a state in which the excitation level has become high and constant. This state is referred to as the extractable state. In the extractable state, the extraction of the beam is started in response to the extraction permission start signal. After the extraction of the beam is stopped in response to the extraction permission end signal (in this embodiment, after the preset time has also elapsed), the beam in the synchrotron 4 is decelerated by lowering the accelerator excitation level, and the preparation for the injection of the next beam is started.

(Case 1: Normal Extraction)

When the charged particle beam generator 1 is in the extractable state, the extraction of the beam is started upon the reception of the extraction permission start signal (S101→S102→S103→S122→S104→S105).

In the spot scanning irradiation method, each spot is irradiated with the beam up to a target dose. After completing the irradiation of a spot (spot irradiation), the next spot irradiation is performed. The spot irradiation is repeated as long as the extraction permission state continues (S105→S204→S205→S206→S207→S208→S209→(iteration of S203-S209)).

(Case 2: Gate OFF→Stoppage of Extraction→Deceleration)

The extraction permission end signal is outputted regularly (periodically) due to a regular (periodical) movement signal. The beam extraction is stopped upon the reception of the extraction permission end signal (S124→S106→S111→S206→S213→(iteration of S204)).

Meanwhile, the extractable state maintaining function 46b operates upon the reception of the extraction permission end signal. Thus, the charged particle beam generator 1 maintains the extractable state until the preset standby time elapses. When the preset standby time elapses without receiving the extraction permission start signal again during the standby time, the extractable state maintaining function 46b finishes its operation and the charged particle beam generator 1 decelerates the beam (S111→(iteration of S112→S113→S114→S112→S113→S110).

(Case 3: Gate OFF→Stoppage of Extraction→Restart of Extraction)

There are also cases where the extraction permission end signal is outputted irregularly during the irradiation. The beam extraction is stopped upon the reception of the extraction permission end signal (S124→S106→S111→S206→S213→(iteration of S204)).

Meanwhile, the extractable state maintaining function 46b operates upon the reception of the extraction permission end signal and the charged particle beam generator 1 maintains the extractable state. When the extraction permission start signal is received again during the standby time, the beam extraction is restarted (S111→(iteration of S112→S113→S114)→S112→S105→S204→S205).

Effect

The effect of this embodiment will be explained below in contrast with the conventional technology. The charged particle irradiation system according to the conventional technology does not have the extractable state maintaining function 46b (characteristic configuration of this embodiment).

Figure 9:
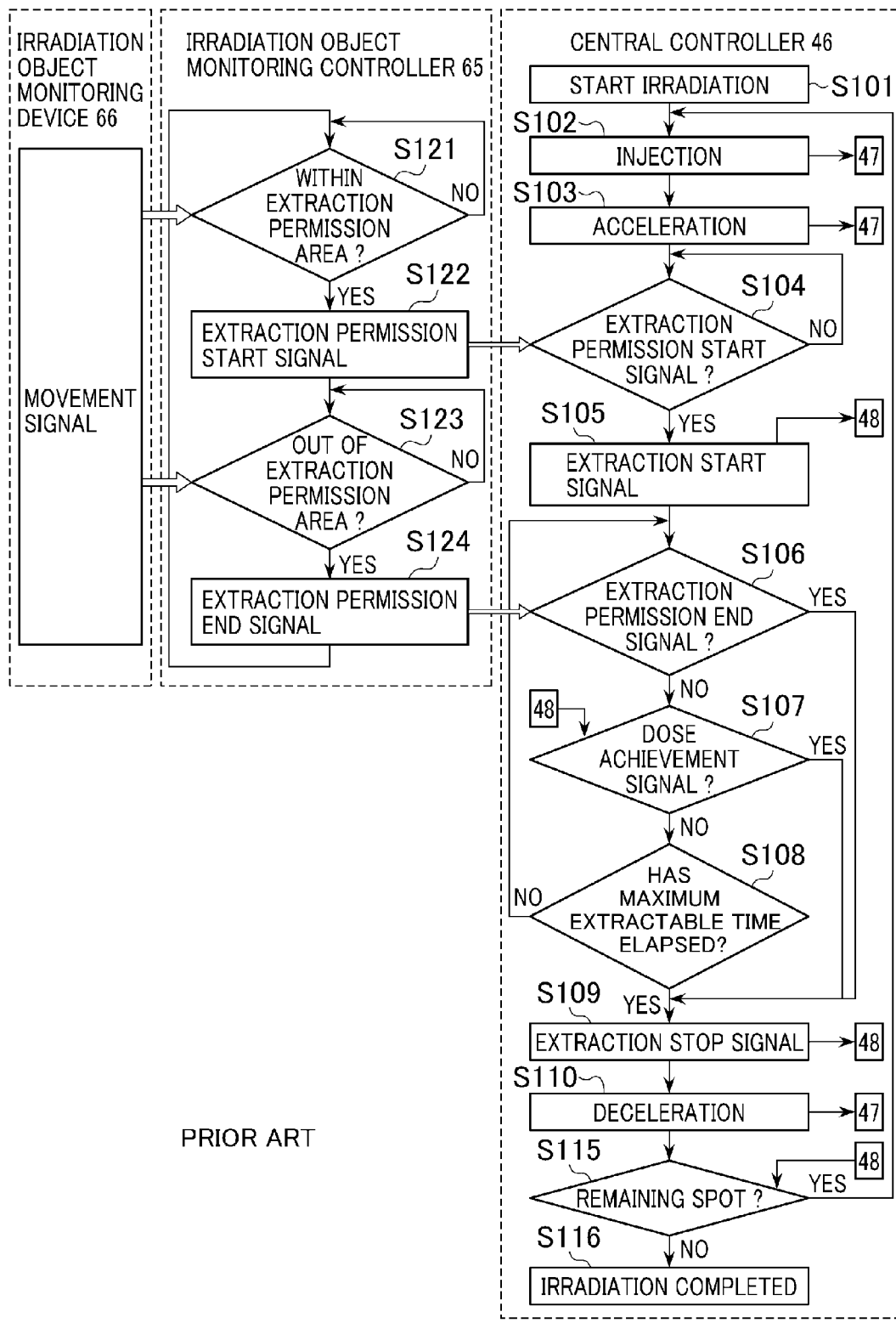
FIG. 9 is a control flow chart showing the details of processing by the central controller (conventional technology).

FIG. 9 is a control flow chart showing the details of the processing by the central controller 46 according to the conventional technology, wherein steps identical to those in FIG. 6 are assigned the same reference characters as in FIG. 6.

During the continuation of the extraction, the central controller 46 judges whether or not the extraction permission end signal has been received from the irradiation object monitoring controller 65 (step S106). If the extraction permission end signal has been received in the step S106, the central controller 46 sends the extraction stop signal to the irradiation controller 48 (step S109) while also sending the deceleration signal to the accelerator controller 47 to decelerate the beam (step S110)

Figure 10:
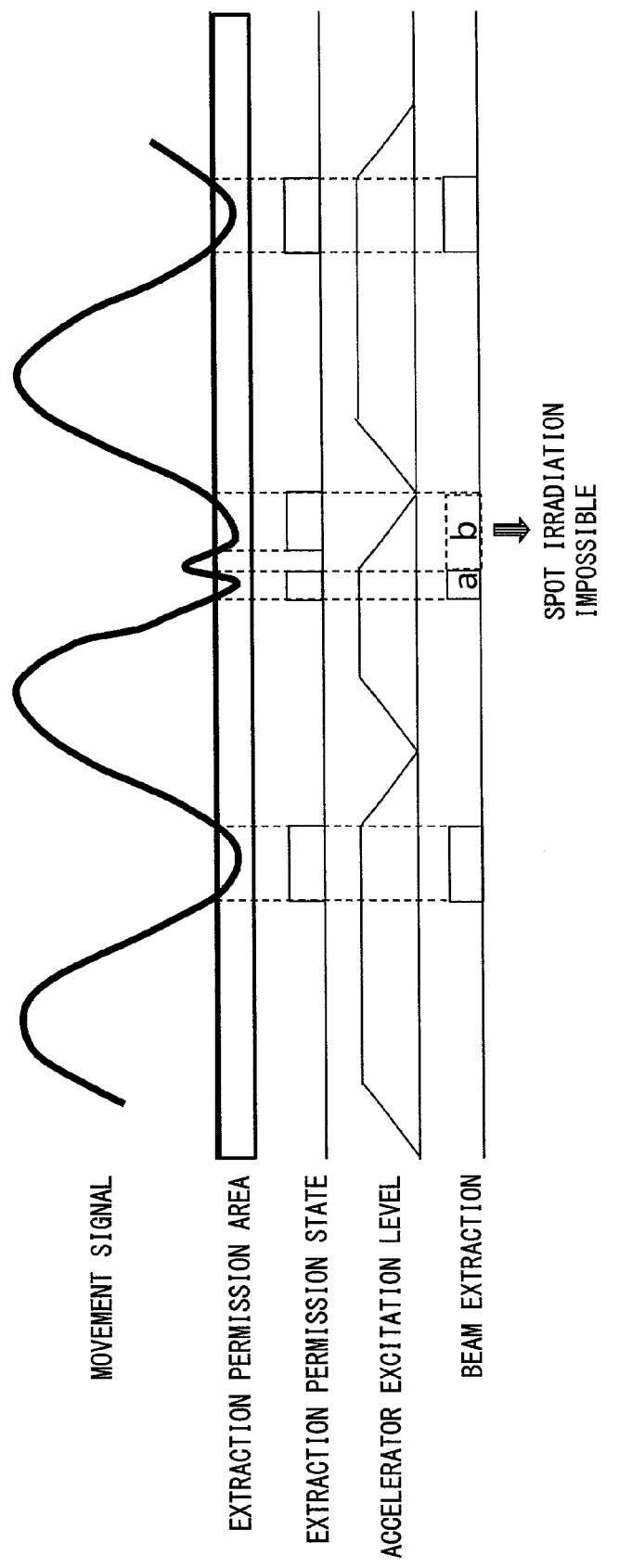
FIG. 10 is a conceptual diagram for explaining the operation of the charged particle irradiation system (conventional technology).

FIG. 10 is a conceptual diagram for explaining the operation of the charged particle irradiation system according to the conventional technology. A case corresponding to the CASE 3 in FIG. 8 will be explained below.

When the charged particle beam generator 1 is in the extractable state, the extraction of the beam is started upon the reception of the extraction permission start signal (S101→S102→S103→S122→S104→S105). The spot irradiation is repeated as long as the extraction permission state continues (S105→S204→S205→S206→S207→S208→S209→(iteration of S203-S209)).

By the above operation, the spot irradiation in the area a in FIG. 10 is carried out.

There are also cases where the extraction permission end signal is outputted irregularly during the irradiation. The beam extraction is stopped upon the reception of the extraction permission end signal (S124→S106→S109→S206→S213→(iteration of S204)).

Meanwhile, upon the reception of the extraction permission end signal, the charged particle beam generator 1 immediately decelerates the beam (S124→S106→S109→S110).

As a result, the spot irradiation in the area b in FIG. 10 cannot be carried out. Since efficient irradiation is impossible as above, the total irradiation time tends to be long, and consequently, the treatment time is liable to be long in the conventional technology.

Returning to FIG. 8, the operation in the case 3 in this embodiment after the restart of the beam extraction will be explained below.

When the extraction permission start signal is received again, the beam extraction is restarted and the spot irradiation is repeated (S112→S105→S204→S205→S209→(iteration of S203-S209)).

The extraction permission end signal is outputted regularly (periodically) due to a regular (periodical) movement signal. The beam extraction is stopped upon the reception of the extraction permission end signal (S124→S106→S111→S206→S213→(iteration of S204)).

As a result, the spot irradiation in the area b' in FIG. 8 is carried out. Owing to the efficient irradiation, the irradiation time and the treatment time can be shortened.

Modifications

The present invention is not to be restricted to the above embodiment; a variety of modifications are possible.

1. Various modifications are possible in regard to the starting point of the operation of the extractable state maintaining function 46b. While the extractable state maintaining function 46b in the above embodiment starts waiting on standby for the preset standby time upon the reception of the extraction permission end signal outputted from the irradiation object monitoring controller 65 in the step S124, the extractable state maintaining function 46b may also be configured to start waiting on standby for the preset standby time upon the transmission of the extraction stop signal to the irradiation controller 48 in the step S111, for example.

2. Various modifications are possible in regard to the setting of the extraction permission state. While the irradiation object monitoring controller 65 in the above embodiment sets the extraction permission state as the state (period) from the outputting of the extraction permission start signal to the outputting of the extraction permission end signal, the extraction permission signal may also be outputted continuously and the extraction permission state may be set as a state (period) from the start of the outputting of the extraction permission signal to the end of the outputting of the extraction permission signal.

3. While the above embodiment has been explained assuming the use of the spot scanning irradiation method as the irradiation method, the embodiment is applicable also to the double scattering irradiation method (broadening the distribution of the beam by using a scatterer) and the wobbler irradiation method (scanning the beam (broadened with a scatterer) in a circular pattern).

<Second Embodiment>

Figure 11:
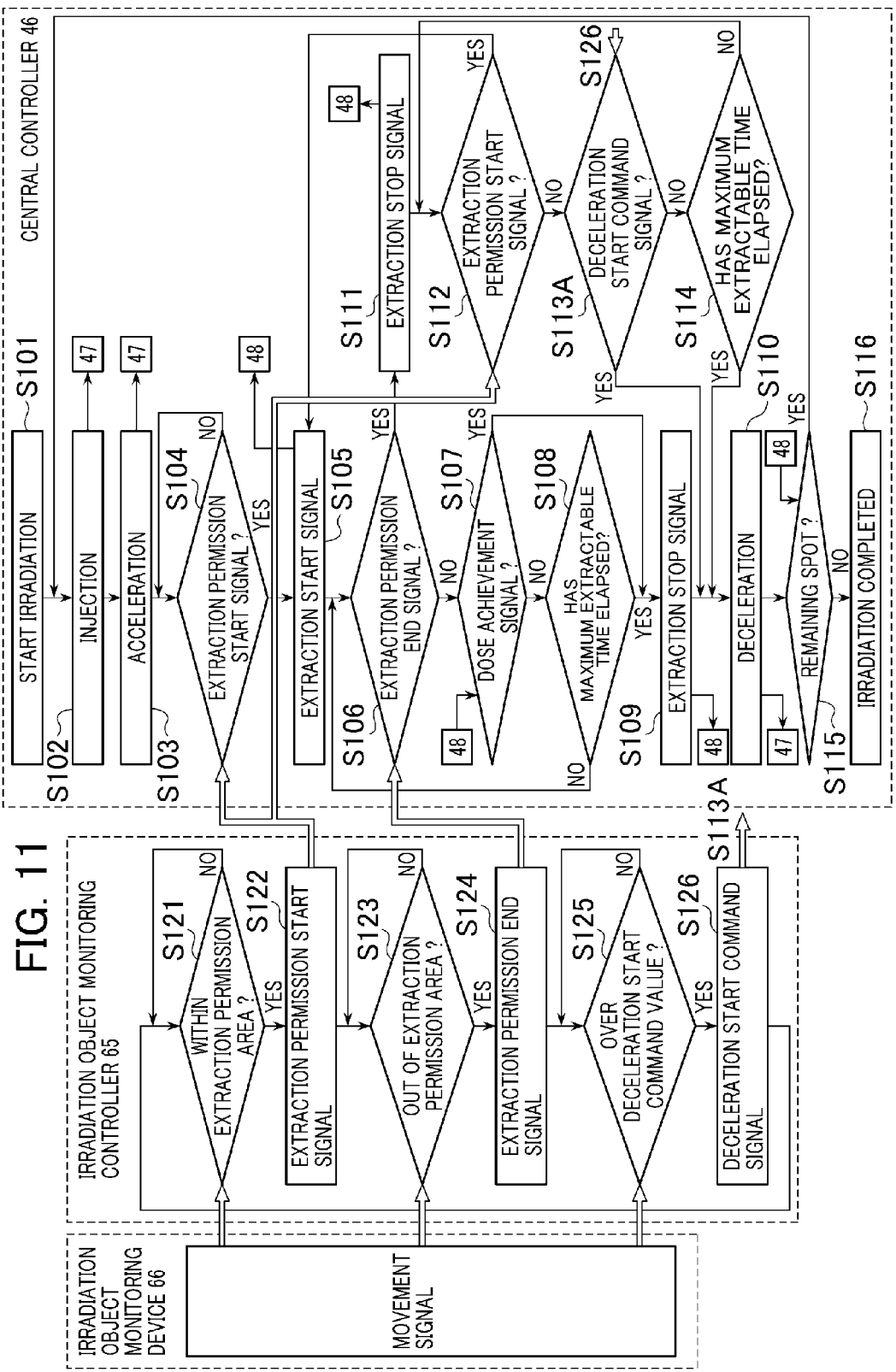
FIG. 11 is a control flow chart showing the details of processing by the central controller (second embodiment).

FIG. 11 is a control flow chart showing the details of the processing by the central controller 46 according to a second embodiment of the present invention, wherein steps identical to those in FIG. 6 are assigned the same reference characters as in FIG. 6.

The extractable state maintaining function 46b in the first embodiment operates just for the preset standby time after the reception of the extraction permission end signal (S113 in FIG. 6). The extractable state maintaining function 46b in the second embodiment may be configured to operate after the reception of the extraction permission end signal until a deceleration start command signal is received, that is, while the movement signal after deviating from the extraction permission area does not exceed a deceleration start command value (S113A in FIG. 11).

After sending the extraction permission end signal to the central controller 46 in the step S124, the irradiation object monitoring controller 65 judges whether or not the movement signal has exceeded the deceleration start command value which has been set outside the extraction permission area (step S125). When the movement signal exceeds the deceleration start command value, the irradiation object monitoring controller 65 sends the deceleration start command signal to the central controller 46 (step S126).

Figure 12:
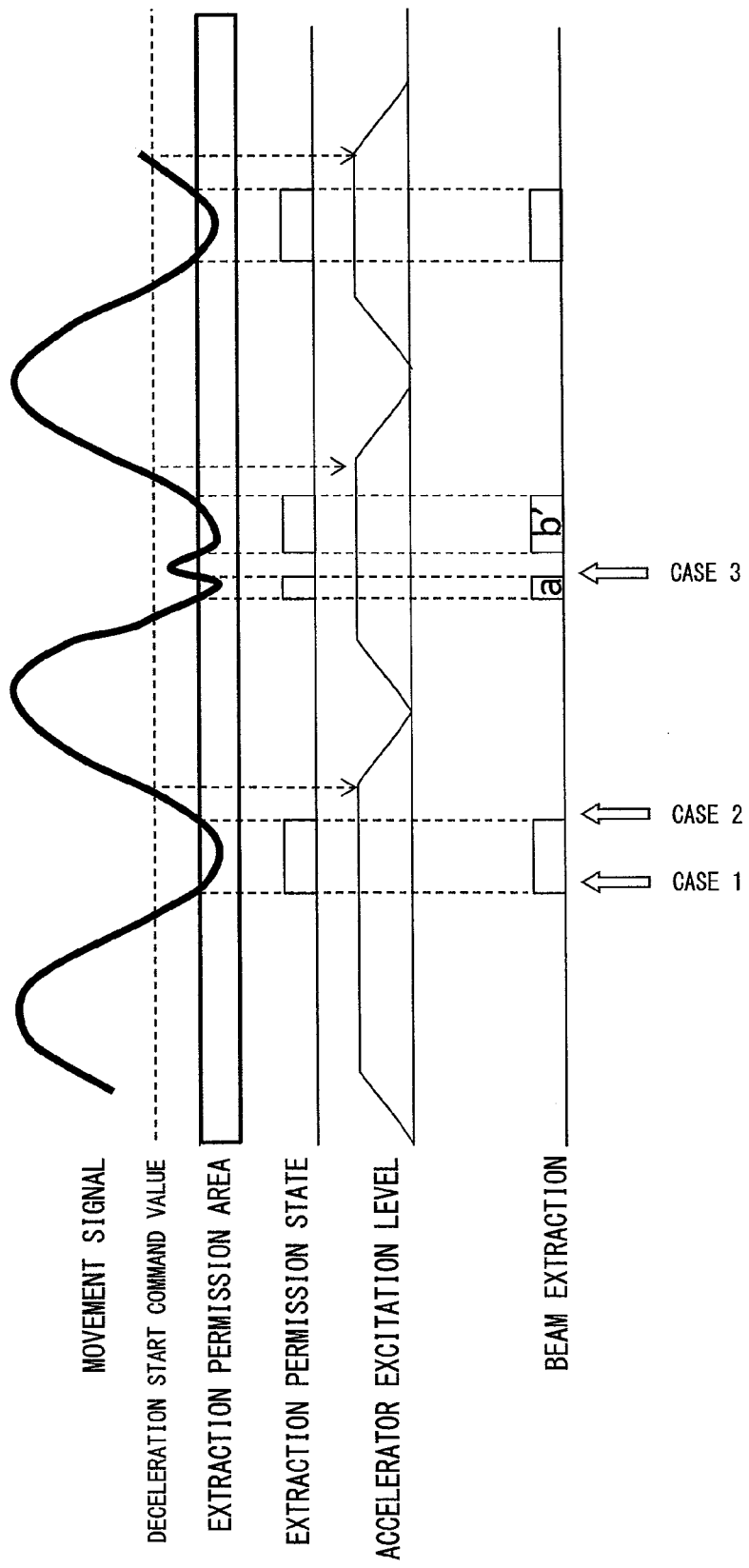
FIG. 12 is a conceptual diagram for explaining the operation of the charged particle irradiation system (second embodiment).

FIG. 12 is a conceptual diagram for explaining the operation of the charged particle irradiation system according to the second embodiment.

The extraction permission state is set in periods during which the movement signal representing the position of the target 37 is within the extraction permission area. The charged particle beam generator 1 accelerates the beam and shifts to the extractable state. The beam extraction is started in response to the extraction permission start signal (case 1).

The beam extraction is stopped in response to the extraction permission end signal. Meanwhile, the extractable state maintaining function 46b operates and the charged particle beam generator 1 maintains the extractable state (standby).

When the movement signal representing the position of the target 37 exceeds the deceleration start command value, the deceleration start command signal is outputted.

When the deceleration start command signal is received without receiving the extraction permission start signal again during the standby time, the extractable state maintaining function 46b finishes its operation and the charged particle beam generator 1 decelerates the beam (case 2).

The beam extraction is stopped during the irradiation due to the reception of the irregular extraction permission end signal. Meanwhile, upon the reception of the extraction permission end signal, the extractable state maintaining function 46b operates and the charged particle beam generator 1 maintains the extractable state. When the extraction permission start signal is received again during the standby time, the beam extraction is restarted (case 3).

The operation of the charged particle irradiation system in the second embodiment is substantially equivalent to that in the first embodiment and effects similar to those of the first embodiment are achieved.

<Third Embodiment>

Figure 13:
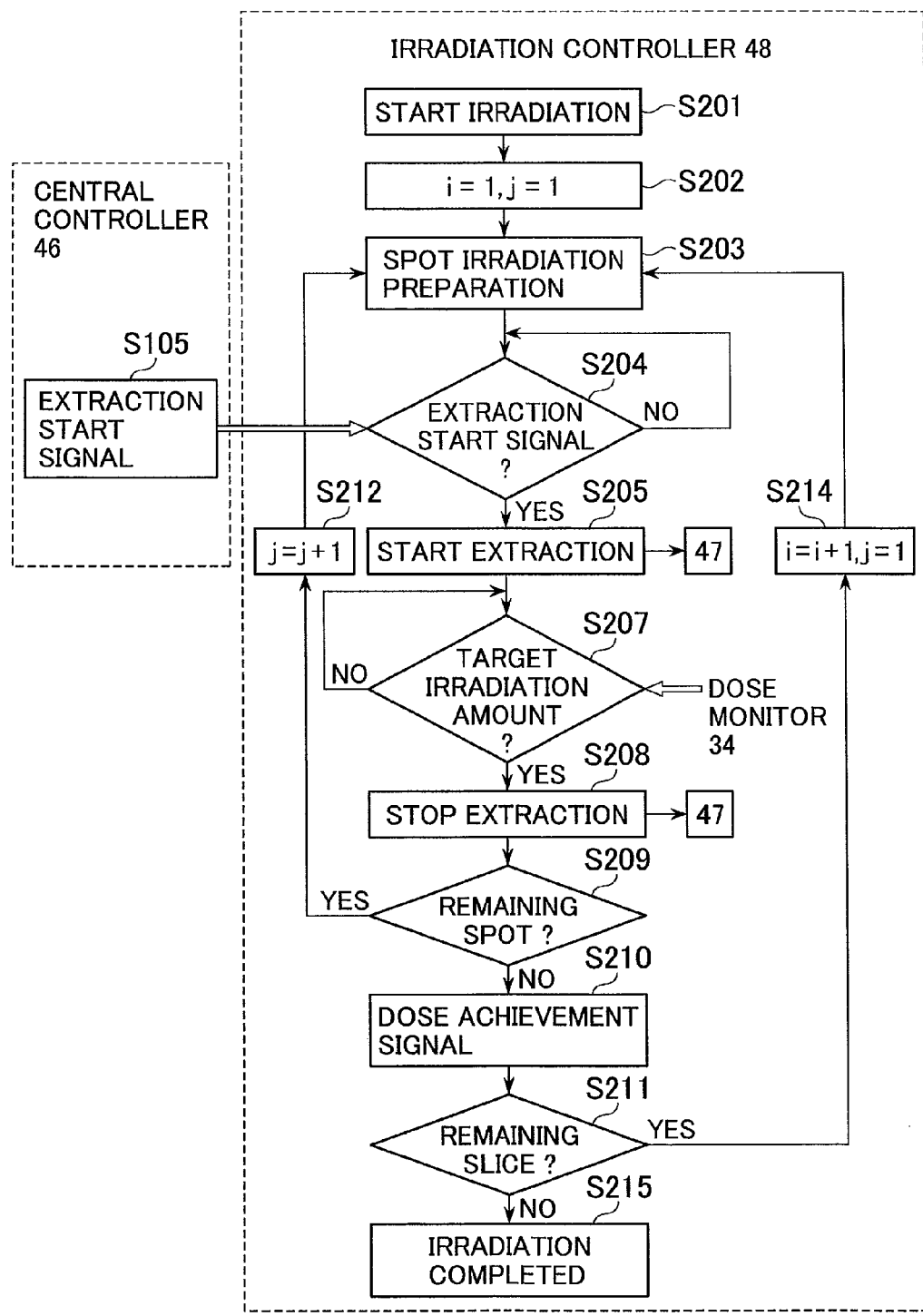
FIG. 13 is a control flow chart showing the details of processing by the irradiation controller (third embodiment).

FIG. 13 is a control flow chart showing the details of the processing by the irradiation controller 48 according to a third embodiment of the present invention, wherein steps identical to those in FIG. 7 are assigned the same reference characters as in FIG. 7.

While the extraction is stopped during the spot irradiation in the first embodiment upon the reception of the extraction stop signal (S206→S213), it is also possible to shift to the standby state after completing the spot irradiation. Thus, the steps S206 and S213 are unnecessary in this embodiment.

In cases where the irradiation time for each spot is short and the movement of the target during the time is negligible, the control can be simplified compared to the first embodiment by not stopping the irradiation in the middle of the spot irradiation.

DESCRIPTION OF REFERENCE CHARACTERS 1 charged particle beam generator
2 beam transport line
3 linear accelerator
4 synchrotron
5 radiofrequency wave application device
6 accelerator 7 control system
8 radiofrequency electrode
9 radiofrequency power supply
11 extraction deflector
12 beam path
14, 15, 16 bending magnet
17 treatment room
21 irradiation nozzle
24 couch
25 irradiation object
31, 32 scanning magnet
33 beam position monitor
34 dose monitor
37 irradiation target
40 X-ray CT device
41 irradiation planning device
42 database
46 central controller
46a gating irradiation function
46b extractable state maintaining function
47 accelerator controller
48 irradiation controller
65 irradiation object monitoring controller
66 irradiation object monitoring device

The invention claimed is:

1. A charged particle irradiation system comprising:
a charged particle beam generator that repeats injection of charged particles, acceleration of the charged particles, an extractable state after finishing the acceleration, and deceleration of the charged particles;
an irradiation nozzle that irradiates an irradiation object with a charged particle beam supplied from the charged particle beam generator; and
a control system that controls the charged particle beam generator and the irradiation nozzle, the control system having:
an irradiation object state variation signal reception function of receiving signals from an irradiation object monitoring device that monitors state variation of the irradiation object;
an extraction permission state setting function of setting an extraction permission state by outputting an extraction permission signal in sync with the state variation of the irradiation object; and
an extraction control function of commanding charged particle beam extraction when the charged particle beam generator is in the extractable state and in the extraction permission state, while commanding stoppage of the charged particle beam extraction when the charged particle beam generator is not in the extraction permission state even if the charged particle beam generator is in the extractable state, wherein:
the control system further has an extractable state maintaining function that operates after the end of the extraction permission state and maintains the extractable state of the charged particle beam generator even after the end of the extraction permission state, and
the extraction control function commands the charged particle beam extraction again when the extraction permission state starts again during the operation of the extractable state maintaining function, while commanding the deceleration of the charged particle beam generator after the end of the operation of the extractable state maintaining function.

2. The charged particle irradiation system according to claim 1, wherein the extractable state maintaining function operates for a preset standby time.

3. The charged particle irradiation system according to claim 2, wherein the extractable state maintaining function starts operating based on a signal that commands termination of the extraction permission state.

4. The charged particle irradiation system according to claim 2, wherein the extractable state maintaining function starts operating based on a signal that commands the stoppage of the charged particle beam extraction.

5. The charged particle irradiation system according to claim 1, wherein the extractable state maintaining function operates only while the state variation of the irradiation object is within a preset range.

6. The charged particle irradiation system according to claim 1, wherein the extraction control function commands the stoppage of the charged particle beam extraction after reception of a signal commanding termination of the extraction permission state and after irradiation with a prescribed dose.

7. A charged particle irradiation method for a charged particle irradiation system equipped with a charged particle beam generator, an irradiation nozzle and a control system that controls the charged particle beam generator, the irradiation nozzle and an irradiation object monitoring device, comprising:
an extraction standby step in which the charged particle beam generator repeats injection of charged particles, acceleration of the charged particles, an extractable state after finishing the acceleration, and deceleration of the charged particles;
an irradiation object state variation monitoring step in which the irradiation object monitoring device monitors state variation of an irradiation object;
an extraction permission state setting step of setting an extraction permission state in sync with the state variation of the irradiation object monitored in the irradiation object state variation monitoring step;
an extraction step of extracting a charged particle beam from the charged particle beam generator and having the irradiation nozzle apply the charged particle beam to the irradiation object when the charged particle beam generator is in the extractable state in the extraction standby step and in the extraction permission state due to the extraction permission state setting step; and
an extraction stoppage step of stopping the extraction when the charged particle beam generator is not in the extraction permission state due to the extraction permission state setting step even if the charged particle beam generator is in the extractable state in the extraction standby step, wherein:
the charged particle irradiation method further comprises an extractable state maintaining step of maintaining the extractable state of the charged particle beam generator even after the extraction permission state ends in the extraction permission state setting step, and
in the extraction step, the charged particle beam is extracted again when the extraction permission state starts again in the extraction permission state setting step during the maintenance of the extractable state by the extractable state maintaining step, and
in the extraction standby step, the charged particle beam generator decelerates the charged particle beam after the end of the maintenance of the extractable state by the extractable state maintaining step.

* * * * *